US00PP35385P2

(12) United States Plant Patent
Bell

(10) Patent No.: US PP35,385 P2
(45) Date of Patent: Sep. 19, 2023

(54) BLUEBERRY PLANT NAMED 'RIDLEY 0803'

(50) Latin Name: ***Vaccinium* hybrid**
Varietal Denomination: Ridley 0803

(71) Applicant: MOUNTAIN BLUE ORCHARDS PTY LTD, Lindendale (AU)

(72) Inventor: Ridley Bell, Lindendale (AU)

(73) Assignee: Mountain Blue Orchards PTY LTD, Lindendale (AU)

( * ) Notice: Subject to any disclaimer, the term of this patent is extended or adjusted under 35 U.S.C. 154(b) by 0 days.

(21) Appl. No.: 17/803,959

(22) Filed: Feb. 7, 2023

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

(56) References Cited

U.S. PATENT DOCUMENTS

| | | | |
|---|---|---|---|
| PP20,695 | P2 | 2/2010 | Wright et al. |
| PP22,778 | P3 | 6/2012 | Wright et al. |
| PP25,432 | P3 | 4/2015 | Bell |
| PP31,035 | P3 | 11/2019 | Bell |
| PP31,074 | P3 | 11/2019 | Bell |

*Primary Examiner* — Karen M Redden
(74) *Attorney, Agent, or Firm* — Plant & Planet Law Firm

(57) ABSTRACT

The new blueberry plant variety 'Ridley 0803' is provided. 'Ridley 0803' is a commercial variety intended for use as fresh fruit for shipping, hand pick, customer pick, machine harvest and processing markets and as a home garden plant. The variety is produced from a cross of 'M09-18-09' (unpatented) and 'Ridley1403' (U.S. Plant Pat. No. 25,432), and can be distinguished by its outstanding features.

5 Drawing Sheets

Latin name of the genus and species: Genus—*Vaccinium*. Species—hybrid.

Variety denomination: The new blueberry plant claimed is of the variety denominated 'Ridley 0803'.

BACKGROUND OF THE INVENTION

The present invention relates to a new and distinct perennial variety of *Vaccinium* hybrid (Southern Highbush Blueberry), which has been given the variety denomination of 'Ridley 0803'. Its market class is that of a fruiting plant. 'Ridley 0803' is intended for use as fresh fruit for shipping, customer pick and processing markets and as a home garden plant.

The new *Vaccinium* hybrid cultivar is a selection resulting from seedlings produced in a breeding program of *Vaccinium* at Lindendale, NSW, Australia in 2013 from the controlled pollination of seed parent 'M09-18-09' (unpatented) with pollen parent 'Ridley 1403' (U.S. Plant Pat. No. 25,432). The seed parent was produced from a seedling selection of seed parent 'C00-09' (U.S. Plant Pat. No. 22,778) and pollen parent 'C99-42' (U.S. Plant Pat. No. 20,695). The pollen parent was produced from a seedling selection of seed parent 'S02-25-05' (not patented) and pollen parent 'S03-08-02' (not patented).

The new cultivar was discovered and selected as a single plant within a population of 100 resulting *Vaccinium* hybrid plants from this controlled pollination in 2016 in a commercial field plantation environment at Tabulam, New South Wales, Australia.

The new blueberry cultivar was designated 'M16-08-03' and has been planted in replicated trials since 2017 at the commercial farms at Tabulam, New South Wales, Australia.

Asexual reproduction of the new cultivar by cutting propagation since 2016 at Lindendale, New South Wales, Australia has demonstrated that the new cultivar reproduces true to type with all of the characteristics, as herein described, firmly fixed and retained through successive generations of such asexual propagation.

SUMMARY OF THE INVENTION

The following are the most outstanding and distinguishing characteristics of the new cultivar when grown under normal horticultural practices in Tabulam, New South Wales, Australia and that have been repeatedly observed and can be used to distinguish 'M16-08-03' ('Ridley 0803') as a new and distinct cultivar of *Vaccinium* hybrid plant:

1. very large fruit size;
2. strong crunch;
3. firm texture;
4. excellent bloom;
5. sweet flavor;
6. vigorous growth;
7. round bush shape; and
8. mid-season timing of flowering and fruiting.

BRIEF DESCRIPTION OF THE DRAWINGS

The accompanying photographic illustration shows typical specimens in full color of the foliage and fruit of the new variety 'Ridley 0803'. The colors are as true as is reasonably possible in a color representation of this type.

The colors in the photographs are as close as possible with the photographic and printing technology utilized. The color values cited in the detailed botanical description accurately describe the colors of the new blueberry.

BRIEF DESCRIPTION OF THE DRAWINGS

The accompanying photographic illustrations show the typical appearance of the new variety 'Ridley 0803'. The colors are as nearly true as is reasonably possible in a color representation of this type. Colors in the photographs may differ slightly from the color values cited in the detailed botanical description which accurately describes the colors of the new plant.

Figure 1:
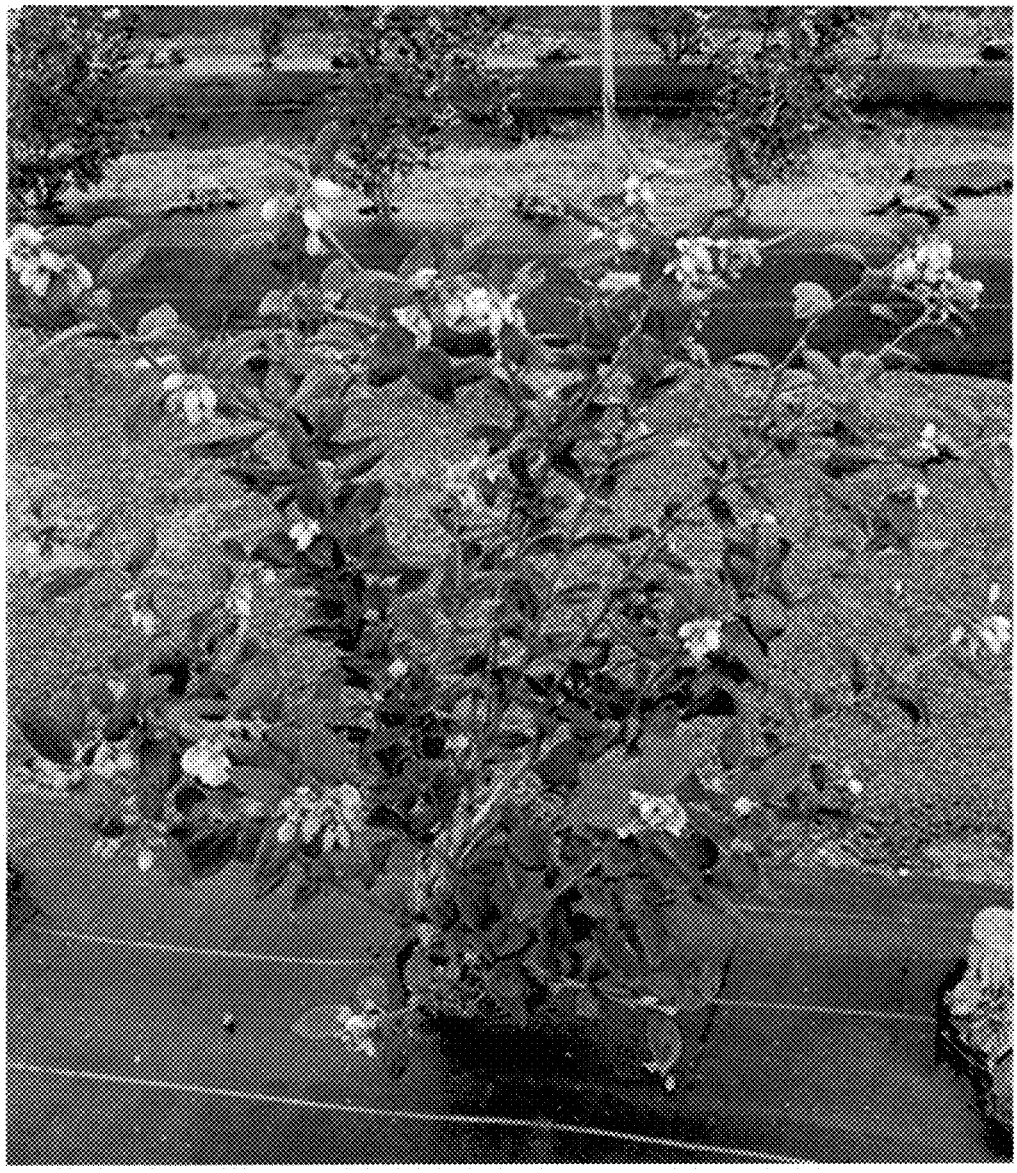

FIG. 1 is a photograph of the new variety 'Ridley 0803', demonstrating the plant's round growth habit.

Figure 2:
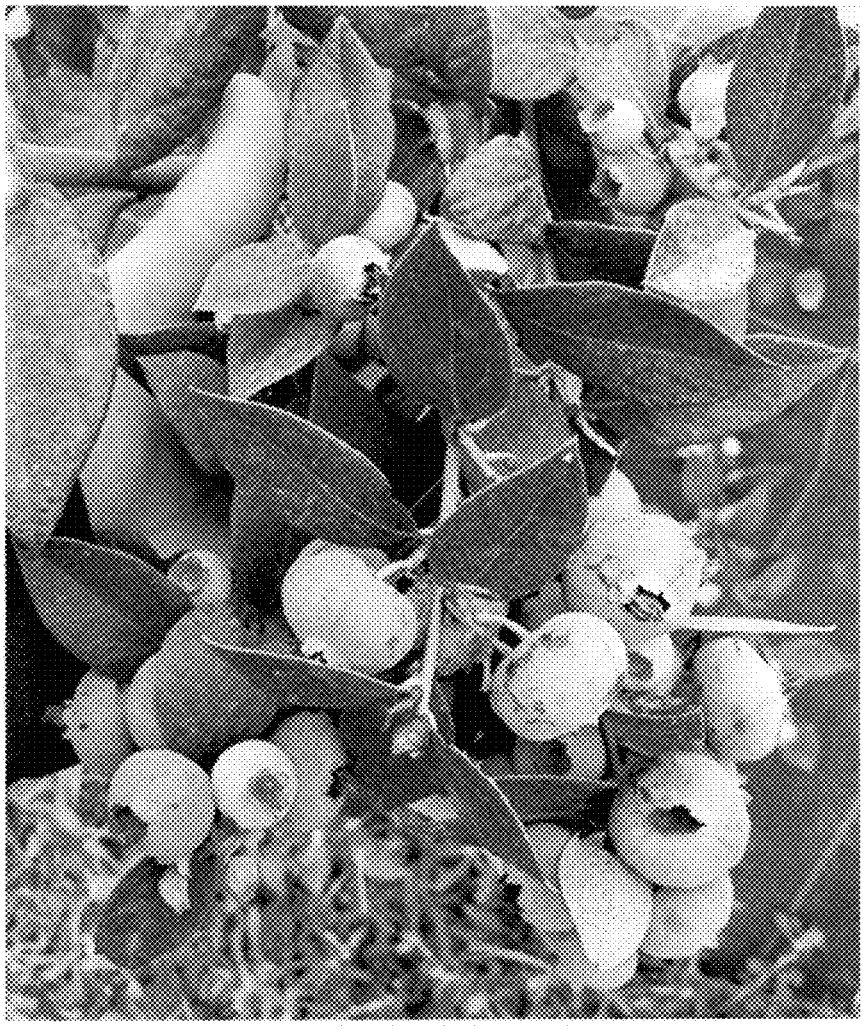

FIG. 2 is a photograph of the fruit of the new variety 'Ridley 0803'.

Figure 3:
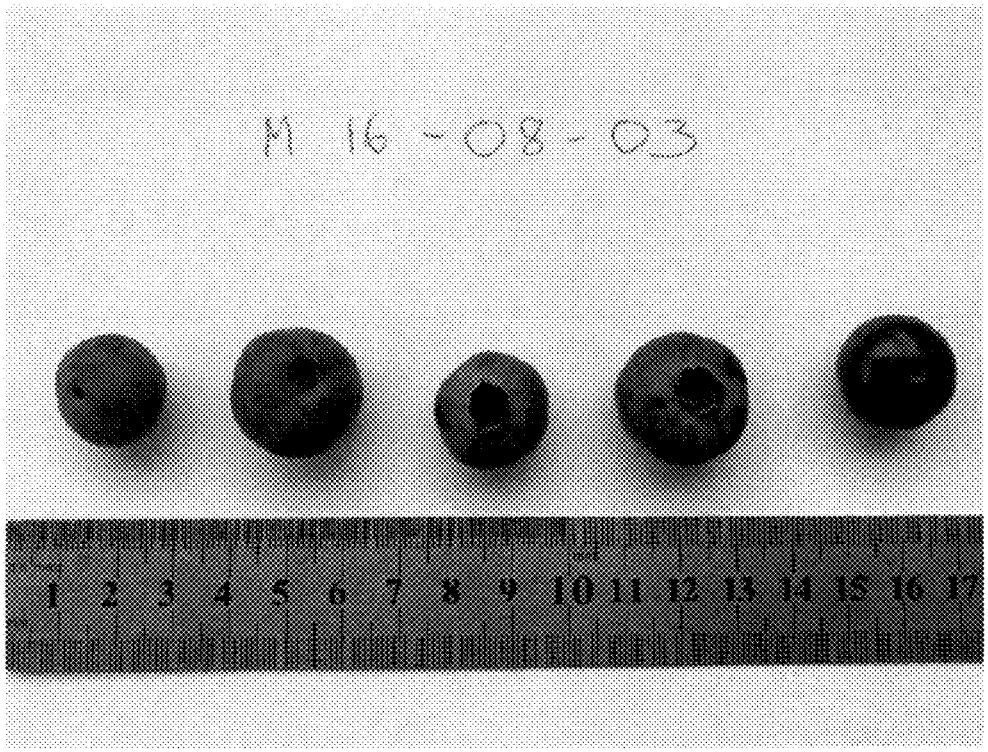

FIG. 3 is a photograph of the fruit of the new variety 'Ridley 0803'.

Figure 4:
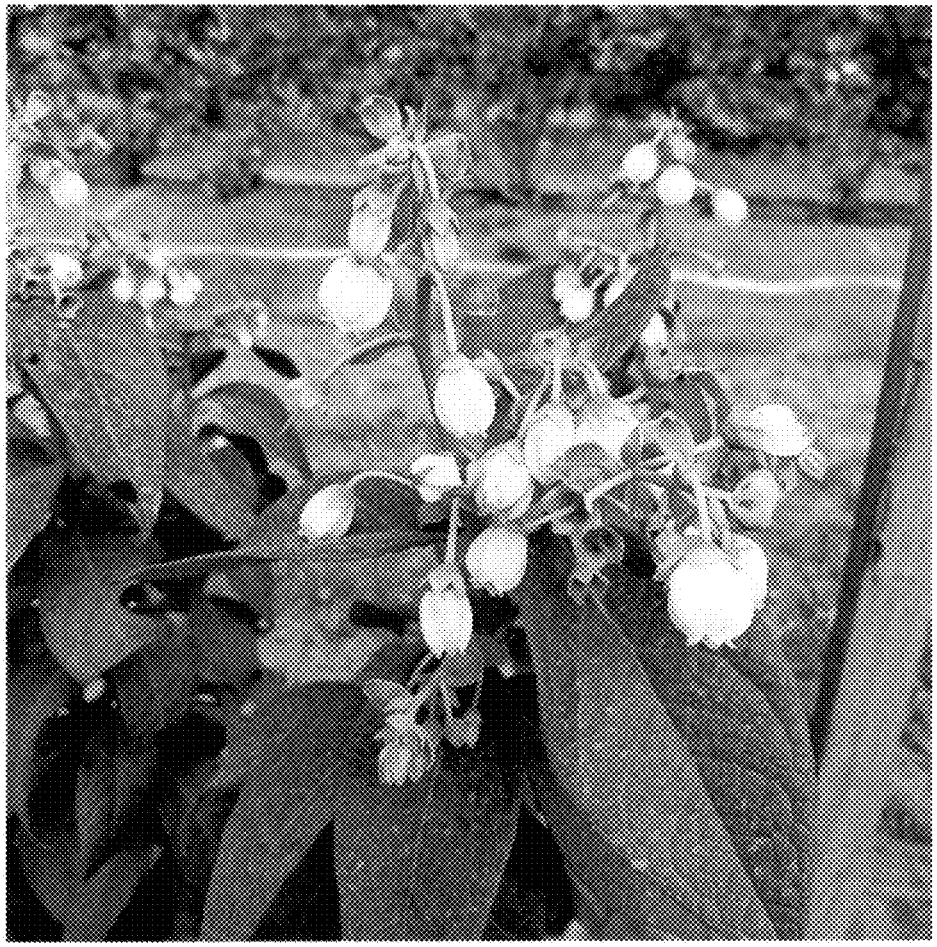

FIG. 4 is a photograph of the flower cluster of the new variety 'Ridley 0803'.

Figure 5:
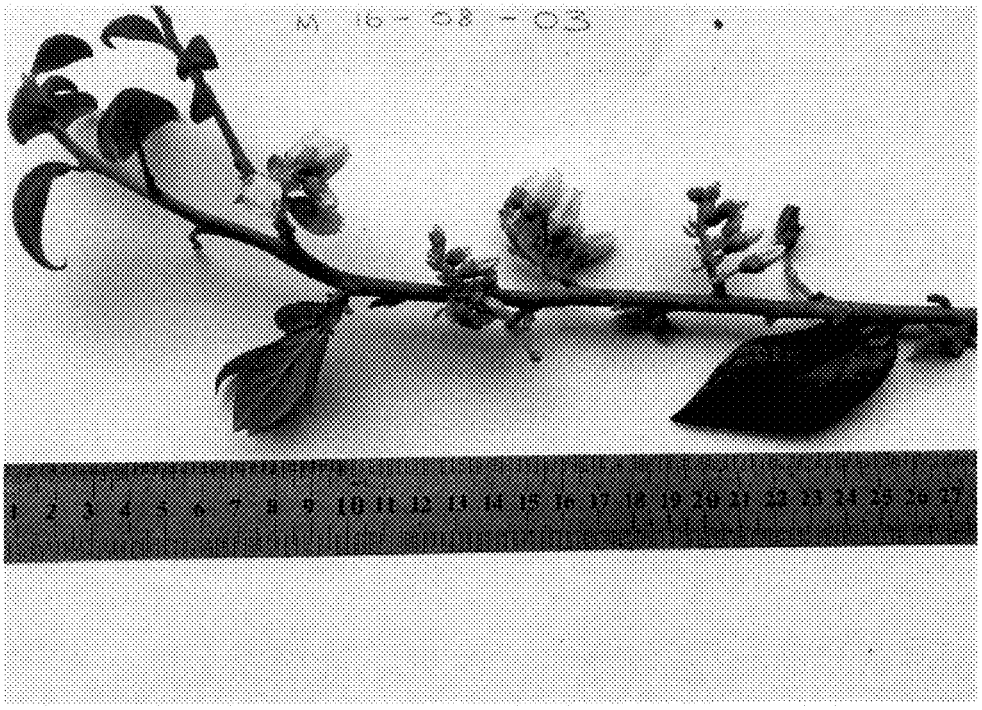

FIG. 5 is a photograph of the flower cluster of the new variety 'Ridley 0803'.

DETAILED BOTANICAL DESCRIPTION

The following detailed description sets forth the distinctive characteristics of 'Ridley 0803'. The data which define these characteristics were collected from asexual reproductions of the original selection. Dimensions, sizes, colors, and other characteristics are approximations and averages set forth as accurately as possible. The plant history was taken on plants approximately 1-2 years of age, and the descriptions relate to plants grown in the field in Tabulam from 2017-2021, New South Wales, Australia. Descriptions of fruit characteristics were made on fruit grown in Tabulam, New South Wales, Australia. Color designations are from Tabulam, New South Wales, Australia. Color notations are based on *The Royal Horticultural Society Colour Chart*, of The Royal Horticultural Society, London, sixth edition.

Classification:

*a. Family.*—Ericaceae.
*b. Genus.*—*Vaccinium.*
*c. Species.*—Hybrid.
*d. Common name.*—Southern Highbush Blueberry.

Parentage:

*Female parent.*—'M09-18-09' (unpatented).
*Male parent.*—'Ridley1403' (U.S. Plant Pat. No. 25,432).

Market class: A fruiting plant intended for use as fresh fruit for shipping, hand pick, customer pick, machine harvest and processing markets and as a home garden plant.

PLANT

General:

*Parentage.*—Female Parent — 'M09-18-09' (unpatented). Male Parent — 'Ridley1403' (U.S. Plant Pat. No. 25,432).
*Plant height.*—Average 1.6 m.
*Plant width.*—Average 1.4 m.
*Growth habit.*—Round.
*Growth.*—Strong.
*Productivity.*—3.7 kg/plant in 2$^{nd}$ harvest.
*Cold hardiness.*—Has not been tested/expected to be low.
*Cold tolerance.*—Has not been tested/expected to be low.
*Chilling requirement.*—Has not been tested/expected to be low.
*Tolerance to disease.*—Has not been tested.
*Leafing.*—Vegetative bud burst is high.
*Twigginess.*—Moderate to high.

STEM

General:

*Suckering tendency.*—Average, 5 canes/plant.
*Mature cane color.*—199D.
*Mature cane length.*—50-90 cm.
*Mature cane width.*—16 mm.
*Bark texture.*—Rough.
*Surface texture of new wood.*—Smooth-medium.
*Internode length on strong, new shoots.*—11-18 mm; 13.5 mm average.
*Fruiting wood.*—Up to 28 cm in length; 15 cm average.

FOLIAGE

General:

*Time of beginning of leaf bud burst.*—Early (from approximately week 35 onwards at Tabulam, NSW, Australia).
*Leaf color* (*top side*).—144A/138A.
*Leaf color* (*under side*).—138B/139D.
*Leaf arrangement.*—Alternate.
*Leaf shape.*—Elliptic.
*Leaf margins.*—Entire.
*Undulation of margin.*—Weak.
*Leaf venation.*—Reticulate.
*Leaf apices.*—Acute.
*Leaf bases.*—Acute.
*Leaf length.*—Average 73 mm.
*Leaf width.*—Average 36 mm.
*Leaf length/width ratio.*—2.0278:1.
*Leaf nectaries.*—Absent.
*Pubescence of upper side.*—Absent.
*Pubescence of lower side.*—Absent.
*Cross sectional profile.*—Flat/slightly curving.
*Longitudinal profile.*—Flat/Straight.
*Attitude.*—Semi-upright.

Petioles:

*Length.*—Average 4.5 mm.
*Width.*—Average 2.3 mm.
*Color.*—145A/B.

FLOWERS

General:

*Time of beginning of flowering.*—Mid (week18-20 at Tabulam, NSW Australia).
*Time of* 50% *anthesis.*—Week 25-27 at Tabulam, NSW Australia.
*Flower shape.*—Urceolate.
*Flower bud density.*—Medium.
*Flower fragrance.*—Absent to weak.

Corolla:

*Color.*—NN155B.
*Length.*—9-12 mm, average 10.7 mm.
*Width.*—8 mm average.
*Aperture width.*—Average 3 mm.
*Anthocyanin coloration of corolla.*—Absent to weak.

*Corolla ridges*.—Present.
*Protrusion of stigma*.—Nil.

Inflorescence:
*Length*.—Average 29.3 mm.
*Diameter*.—Average 21.5 mm.
*Length of peduncle*.—Average 16.9 mm.
*Surface texture of peduncle*.—Smooth.
*Color of peduncle*.—142C.
*Length of pedicel*.—6 mm average.
*Surface texture of pedicel*.—Smooth.
*Color of pedicel*.—142C.
*Number of flowers per cluster*.—Average 8.
*Flower cluster density*.—Medium.

Calyx (with sepals):
*Diameter*.—Average 7.2 mm.
*Color* (*sepals*).—142C.

Stamen:
*Length*.—7 mm.
*Number per flower*.—8-10.
*Filament color*.—150D.

Pistil:
*Length*.—11 mm.
*Style length*.—9-10 mm.
*Ovary color* (*exterior*).—147A.

Anther:
*Length*.—4.6 mm.
*Number*.—8-10.
*Color*.—N163A/N167A.

Pollen:
*Abundance*.—High.
*Color*.—158C.
*Self-compatibility*.—Low — moderate 40%.

FRUIT

General:
*Time of fruit ripening*.—Mid season (from week 30 in Tabulam, NSW, Australia).
*Time of* 50% *maturity*.—Week 40 at Tabulam, NSW, Australia.
*Fruit development period*.—77-91 days.
*Cluster density*.—Medium.
*Unripe fruit color*.—145A.
*Ripe berry color*.—202A/203D.
*Berry surface wax abundance*.—Strong.
*Berry flesh color*.—157B/191B.
*Berry weight*.—4.1 gram average.
*Berry height from calyx to scar*.—13.4 mm average.
*Berry diameter*.—22 mm average.
*Berry shape*.—Oblate.
*Fruit stem scar*.—Small (dry).
*Sweetness when ripe*.—14° Bx.
*Firmness when ripe*.—Firm (64% Durofel).
*Acidity when ripe*.—Low to moderate.
*Storage quality*.—Performs adequately in storage trials for up to 4 weeks.
*Suitability for mechanical harvesting*.—Very suitable.
*Self-fruitfulness*.—Low to moderate, requires cross pollination.(40%).
*Uses*.—Fresh fruit for shipping, customer pick and processing markets and as a home garden plant.

SEED

General:
*Seed abundance in fruit*.—Not assessed.
*Seed color*.—Not assessed.
*Seed dry weight*.—Not assessed.
*Seed length*.—Not assessed.

COMPARISON BETWEEN PARENTAL AND COMMERCIAL CULTIVARS

When 'Ridley 0803' is compared to the seed parent 'M-09-18-09' (unpatented) it can be observed that 'M-09-18-09' has comparatively poor flavor, firmness and plant vigor. 'M-09-18-09' has not been maintained so is not available for further comparison.

Table 1, below, provides comparisons between 'Ridley 0803', its pollen parent, 'Ridley 1403', and the commercial cultivars that it has the most similarity to, 'Ridley 0808' (U.S. Plant Pat. No. 31,074) and 'Ridley 1607' (U.S. Plant Pat. No. 31,035).

TABLE 1

| Organ | Context | 'Ridley 0803' | 'Ridley 1403' U.S. Plant Pat. No. 25,432) |
|---|---|---|---|
| Plant | Vigor | Strong | Strong |
| Plant | Growth habit | Round | Upright to semi-upright |
| One-year-old shoot | Color | Green | Green |
| One-year-old shoot | Length of internode | Medium | Medium |
| Leaf | Length | Long to very long | Long to very long |
| Leaf | Width | Broad | Broad |
| Leaf | Shape | Elliptic | Elliptic |
| Leaf | Color of upper side | Green | Green |
| Leaf | Intensity of green color on upper side (varieties with green leaf color only) | Medium | Medium |
| Leaf | Margin | Entire | Entire |
| Flower bud | Anthocyanin coloration | Weak | Weak |
| Flower | Shape of corolla | Urceolate | Urceolate |
| Flower | Size of corolla tube | Medium | Medium to large |
| Flower | Anthocyanin coloration of corolla tube | Absent or very weak | Absent or very weak |
| Flower | Ridges on corolla tube | Present | Present |
| Fruit cluster | Density | Medium | Medium to dense |
| Unripe fruit | Intensity of green color | Light | Light |
| Fruit | Size | Very large | Very large |
| Fruit | Shape in longitudinal section | Oblate | Round |
| Fruit | Attitude of sepals | Erect | Erect |
| Fruit | Diameter of calyx basin | Large | Large |
| Fruit | Depth of calyx basin | Deep | Deep |
| Fruit | Intensity of bloom | Strong | Medium |
| Fruit | Color of skin | Dark blue | Dark blue |
| Fruit | Firmness | Firm to very firm | Very firm |
| Fruit | Sweetness | High | High |
| Fruit | Acidity | Low to medium | Low |
| Time of | Vegetative bud burst | Early to medium | Early to medium |
| Time of | Beginning of flowering | Medium | Early to medium |

TABLE 1-continued

| | | | |
|---|---|---|---|
| | ripening | | medium |
| Organ | Context | 'Ridley 0808' (U.S. Plant Pat. No. 31,074) | 'Ridley 1607' U.S. Plant Pat. No. 31,035) |
| Time of | Beginning of fruit ripening | Medium | Early to medium |
| Plant | Vigor | Strong | Strong to very strong |
| Plant | Growth habit | Upright | Upright to semi-upright |
| One-year-old shoot | Color | Green | Green |
| One-year-old shoot | Length of internode | Medium-long | Medium |
| Leaf | Length | Medium to long | Long |
| Leaf | Width | Broad | Broad |
| Leaf | Shape | Elliptic | Elliptic |
| Leaf | Color of upper side | Green | Green |
| Leaf | Intensity of green color on upper side (varieties with green leaf color only) | Medium | Medium |
| Leaf | Margin | Entire | Entire |
| Flower bud | Anthocyanin coloration | Medium | Weak |
| Flower | Shape of corolla | Urceolate | Urceolate |
| Flower | Size of corolla tube | Medium | Medium |
| Flower | Anthocyanin coloration of corolla tube | Absent or very weak | Absent or very weak |

TABLE 1-continued

| | | | |
|---|---|---|---|
| Flower | Ridges on corolla tube | Present | Present |
| Fruit cluster | Density | Medium | Medium |
| Unripe fruit | Intensity of green color | Light | Light |
| Fruit | Size | Medium to large | Medium to large |
| Fruit | Shape in longitudinal section | Oblate | Oblate |
| Fruit | Attitude of sepals | Erect | Erect |
| Fruit | Diameter of calyx basin | Large to very large | Large to very large |
| Fruit | Depth of calyx basin | Deep | Deep |
| Fruit | Intensity of bloom | Strong | Strong |
| Fruit | Color of skin | Dark blue | Dark blue |
| Fruit | Firmness | Very firm | Very firm |
| Fruit | Sweetness | Very high | High to very high |
| Fruit | Acidity | Medium to high | Medium |
| Time of | Vegetative bud burst | Medium to late | Early |
| Time of | Beginning of flowering | Very late | Late to very late |
| Time of | Beginning of fruit ripening | Very late | Late to very late |

The invention claimed is:

1. A new and distinct variety of blueberry plant named 'Ridley 0803', substantially as illustrated and described herein.

* * * * *